United States Patent [19]

Forestier et al.

[11] Patent Number: 4,839,160
[45] Date of Patent: Jun. 13, 1989

[54] POLYMERS CAPABLE OF ABSORBING ULTRAVIOLET RADIATION, THEIR PREPARATION AND THEIR USE IN COSMETIC COMPOSITIONS

[75] Inventors: Serge Forestier, Claye Souilly; Claude Mahieu, Paris, both of France

[73] Assignee: L'Oreal, Paris, France

[21] Appl. No.: 30,071

[22] Filed: Mar. 25, 1987

[30] Foreign Application Priority Data

Mar. 28, 1986 [FR] France .................. 86 04544

[51] Int. Cl.$^4$ .......................... A61K 7/40; A61K 7/42; A61K 7/44
[52] U.S. Cl. .................. 424/59; 424/DIG. 5; 424/47; 514/937; 514/938; 514/939
[58] Field of Search .......................... 424/59

[56] References Cited

U.S. PATENT DOCUMENTS

| | | | |
|---|---|---|---|
| 3,980,617 | 9/1976 | Jacquet et al. | 424/60 |
| 4,166,109 | 8/1979 | Jacquet et al. | 424/59 |
| 4,233,430 | 11/1980 | Jacquet et al. | 424/59 |
| 4,250,108 | 2/1981 | Bouillon et al. | 424/59 |

*Primary Examiner*—Dale R. Ore
*Attorney, Agent, or Firm*—Cushman, Darby & Cushman

[57] ABSTRACT

An ultraviolet radiation absorbing polymer having units of formula I:

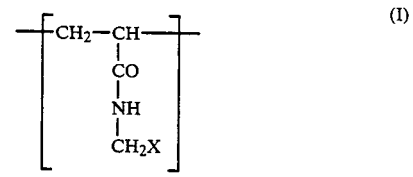

wherein
X is a group derived from benzylidene-bornanone of formula II

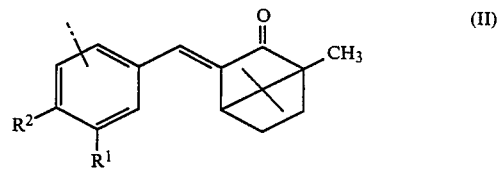

wherein
$R^1$ represents hydrogen or $C_1$–$C_{12}$ alkoxy and
$R^2$ represents $C_4$–$C_{12}$ alkyl.

The polymer is useful in protecting human skin against sunburn.

9 Claims, No Drawings

POLYMERS CAPABLE OF ABSORBING ULTRAVIOLET RADIATION, THEIR PREPARATION AND THEIR USE IN COSMETIC COMPOSITIONS

The present invention relates to new polymers capable of absorbing ultraviolet rays, to their preparation and to their use principally in cosmetic compositions.

It is known that exposure of the human body to ultraviolet rays, and in particular to sun rays, causes erythema of the skin which can result, in certain cases, to burns of relatively significant intensity. It is also known that the ultraviolet rays responsible for these effects are those whose wavelength is between about 280 and 315 nm.

To avoid these deleterious effects, cosmetic compositions have been employed which contain substances capable of absorbing ultraviolet rays in the wavelength the zone of 280-315 nm so as to protect the skin against solar erythema while at the same time permitting a tanning of the skin, since these compounds do not absorb the ultraviolet rays responsible for tanning, i.e. those whose wavelength extends in the zone of 315 to 400 nm.

It has been observed, however, that with certain persons having sensitive skin, ultraviolet rays whose wavelength is between about 315 and 340 nm cause or amplify an erythematous reaction.

Moreover, it is known that to avoid, principally, penetration of ultraviolet-absorbing substances in the organism through the epidermis, the production of polymers capable of absorbing ultraviolet by fixing these substances onto macromolecular chains has been proposed.

It has now been discovered that new ultraviolet absorbing polymers can be prepared whose maximum absorption is situated in the wavelength zone of 315-340 nm, these polymers being compatible with cosmetic composition formulations which are applicable to the skin. These new polymers can then be included in highly protective cosmetic composition formulations which are useful not only for subjects with sensitive skin, but also for normal subjects in the case of intense exposure to solar rays.

In French patent application No. 2,430,938, there is described sunscreen cosmetic compositions containing acrylamidomethyl polymers whose lateral chain carries nonsubstituted benzylidene-camphor groups. These polymers must be used in a relatively significant concentration in the composition in order to obtain a high protection index. However, such compositions exhibit certain disadvantages in that, in particular, they create a disagreeably sticky feel during application, as well as a sensation of discomfort after application. To avoid these disadvantages, it was necessary to prepare the polymer under special conditions in a manner to avoid the formation, or to eliminate, polymeric fractions of high molecular weight.

It has now been discovered, in a surprising manner, that polymers of the present invention which are derived from substituted benzylidene-camphor do not exhibit these disadvantages. It is possible to preserve the fractions of high molecular mass without harming the ease of formulating the composition or reducing the comfort of applying the composition to the skin. Moreover, the polymers of the present invention do not manifest any toxicity on application to the skin or even when administered orally, whereas the corresponding alkoxybenzilidene camphor precursors have a certain toxicity when administered orally.

The new polymers of the invention contain units of formula I $$\left[ \begin{array}{c} CH_2-CH- \\ | \\ CO \\ | \\ NH \\ | \\ CH_2X \end{array} \right] \quad (I)$$

wherein

X is a group derived from benzylidene bornanone of formula II:

<chemical structure (II)> wherein $R^1$ represents hydrogen or a $C_1-C_{12}$ alkoxy group and
$R^2$ represents a $C_4-C_{12}$ alkoxy group.

Representative polymers of the present invention include, in particular:

those which contain units of formula I for which $R^1$ represents hydrogen or a methoxy or butoxy group; and those for which $R^2$ represents butoxy, hexyloxy, octyloxy or dodecyloxy.

The group X is attached to the lateral chain of units I in the 2' or 3' position.

The polymers of the present invention have an average molecular weight generally ranging between 1,000 and 1,000,000 and preferably between 1,500 and 100,000.

the polymers of the present invention can be either homopolymers, or copolymers, the said copolymers being on the one hand those which contain only units of formula I, but which contain at least two different types of units of formula I (i.e. they have different values of X) and on the other hand, copolymers containing both units of formula I and other analogous units such as those of formula I' defined below, which are capable of absorbing ultraviolet radiation.

The polymers of the present invention contain at least 5 mole percent and, preferably, at least 10 mole percent of units of formula I.

Representative copolymers of the present invention containing units, other than those of formula I, which are capable of absorbing ultraviolet rays, include, in particular, those which contain units of formula I':

$$\left[ \begin{array}{c} CH_2-CH- \\ | \\ CO-NH-CH_2-X^1 \end{array} \right] \quad (I')$$

wherein $X^1$ represents a group derived from bornanone of formula II':

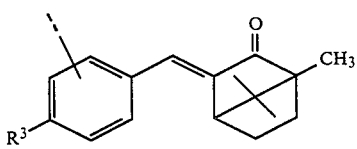

wherein $R^3$ represents hydrogen or $C_1-C_4$ alkyl.

The respective molar proportions of units of formulas I and I' can range for example, from 5:95 to 95:5.

The introduction of units of formula I' permits principally to extend the wavelength range of U.V. radiations absorbed by the polymers, toward UVB.

The present invention also relates to a process for preparing the polymers defined above.

This process comprises preparing a "monomer-filter" of formula IV:

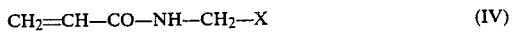

$$CH_2=CH-CO-NH-CH_2-X \quad (IV)$$

wherein X is defined above and homopolymerizing the said monomer-filter or copolymerizing the said monomer-filter with at least one other ethylenically unsaturated comonomer capable of absorbing ultraviolet rays.

The polymerization reaction can be effected in accordance with conventional poymerization methods, i.e. in mass, in solution, in suspension or in emulsion, by using a polymerization initiator. The reaction is effected, preferably, in solution or in suspension.

The polymerization initiators are, in general, known radical polymerization initiators. Their choice depends principally on the different monomers used and the reaction medium employed.

Representative useful initiators include peroxides such as benzoyl peroxide, lauroyl peroxide, acetyl peroxide, tert. butyl hydroperoxide, benzoyl hydroperoxide and $H_2O_2$ as well as such initiators as azobisisobutyronitrile, oxido-reduction initiation systems including sodium persulfate coupled to sodium bisulfite, or even the oxido-reductor system constituted by the $H_2O_2$-ascorbic acid couple. The concentration of the initiator is generally between 0.2 and 35 percent and preferably between 0.5 and 20 percent by weight relative to the total weight of the monomers.

The molar mass of the polymers can be regulated by any known method, for example, by dilute solution polymerization, by polymerization in the presence of significant amounts of initiator or by introducing chain regulating agents, and the like.

To prepare the monomer-filters of formula IV N-hydroxymethyl acrylamide is reacted with a benzylidene bornanone derivative of formula V:

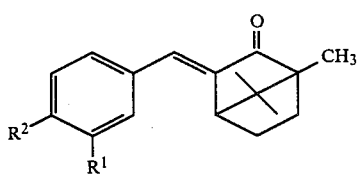

wherein $R^1$ and $R^2$ have the meaning given above.

This reaction is conducted under conditions conventional for a Friedel-Crafts alkylation reaction, in the presence of an acid catalyst such as sulfuric acid.

The position of the substituent introduced depends on the nature of the substituent $R^1$. When $R^1$ represents hydrogen, the acrylamidomethyl substituent is introduced at position 3'. When $R^1$ represents a $C_1-C_{12}$ alkoxy group, the acrylamidomethyl substituent is introduced at position 2'.

The monomers of formula IV':

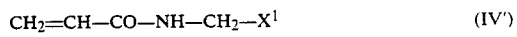

$$CH_2=CH-CO-NH-CH_2-X^1 \quad (IV')$$

wherein $X^1$ is defined above, are prepared in a manner analogous to that described for the monomers of formula IV.

The invention also relates to a means for practicing the process of the invention, this means comprising the derivatives of formulas IV and IV'.

The benzylidene bornanone derivatives of formula V, employed as starting products in the process of the present invention, can be obtained, for example, in accordance with the process described in French patent application No. 78.20701 (publication No. 2,430,938).

The bornanone derivatives of formula V':

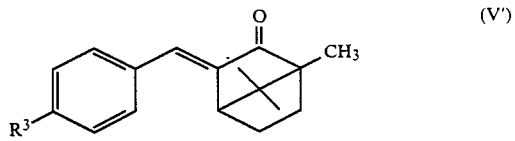

can be prepared, for example, in a manner analogous to that described in French Pat. No. 2,111,757.

As indicated above, the polymers containing units of formula I can be used as protection agents against ultraviolet radiations, and in particular in the preparation of cosmetic compositions intended to protect the skin against sunburn. In addition to an interesting protective effect, these polymers are well adapted to the production of cosmetic formulations for protection of the skin against the effects of exposure to the sun. They possess principally good solubility in oily excipients such as, for example, benzoates of higher fatty alcohols (principally benzoates of $C_{12}-C_{15}$ fatty alcohols).

These polymers absorb ultraviolet rays in the wavelength zones ranging from 280 to 370 nm. This absorbtion is a function essentially of the nature of the substituent $R^1$.

Thus, when $R^1$ represents hydrogen, the polymer, based on the formula I units, absorbs ultraviolet rays in a wavelength zone ranging from 280 to 350 nm, with a maximum absorption at about 315 nm.

When $R^1$ represents an alkoxy group, the polymer absorbs ultraviolet rays in the wavelength zone ranging from about 280 to 370 nm, with a maximum absorption at about 335 nm.

The present invention also relates to a cosmetic composition for protection against ultraviolet radiation, characterized by the fact that they include as an active component at least one polymer, such as defined above, containing units of formula I.

These compositions can be provided in the form of aqueous or hydroalcoholic solutions, oily solutions or emulsions, or even in the form of sticks. Moreover, they can be packaged, in combination with a propellant, in containers suitable for pressurized aerosol compositions.

The cosmetic compositions of the present invention can contain, in addition to the ultraviolet absorbing polymers, various adjuvants conventionally present in cosmetic compositions of this type, for example hydrating agents, emollients or thickening agents, surfactants, preservatives, perfumes, dyes, etc.

In the composition of the present invention, the polymers containing units of formula I are generally present in an amount ranging from 0.2 to 20 weight percent based on the total weight of the composition.

Previously, the absorbent strength of the filter was expressed using the value of Ksp (K specific) which is a function (1) of the amount of filtering substance contained in the sample, (2) of the optical density measured and (3) of a constant relating to the apparatus.

The definition of Ksp is given in "Introduction to Electronic Absorption Spectroscopy In Organic Chemistry" by Gillian and Stern, Arnold Ed., London 1954, page 10.

$$Ksp = \frac{K}{C} \text{ with } K = \frac{d}{l}, \text{ wherein}$$

$d$ = measured optical density, $c$ = concentration of the solution, g/ml; and $l$ = thickness of the cell, in cm.

Actually, the absorbent strength is defined by the term "specific absorbance, $a_s$", defined by the Norme Francaise T.01030 (January 1972) which is related to Ksp by the equation:

$$\frac{Ksp}{a_s} = 1000$$

In the present specification the absorbent strength is expressed by means of specific absorbance.

The following nonlimiting examples illustrate the present invention.

EXAMPLE 1

Preparation of 2'-acrylamidomethyl-4'-butoxy-5'-methoxy-3-benzylidene camphor (a) Preparation of 4'-butoxy-3'-methoxy-3-benzylidene camphor There are heated for one hour at 80° C., 182.68 g of camphor and 71.29 g of sodium methylate in one liter of toluene. 249.9 g of 4-butoxy-3-methoxy benzaldehyde are added and the reaction mixture is then heated at reflux for 2.5 hours.

After cooling, the reaction mixture is poured into 1.5 liters of water. The organic phase is decanted, washed with water, then dried on sodium sulfate. After evaporation of the toluene under reduced pressure, the oily residue is recrystallized in a 25:75 water-isopropanol mixture, yielding 164 g of the expected product in the form of white cyrstals having the following properties:

| Melting point: 62° C. | | |
|---|---|---|
| Elemental Analysis: | | |
| | C | H |
| Calculated | 77.19 | 8.17 |
| Found | 77.22 | 8.75 |
| U.V. Spectra (Methanol) | | |
| λ max: 330 nm | | |
| ε: 20900 | | |

(b) Preparation of 2'-acrylamido-4'-butoxy-5'-methoxy-3-benzylidene camphor

At 0° C., 500 cm³ of concentrated sulfuric acid are mixed with 500 cm³ of acetic acid. There are slowly introduced with stirring while maintaining the temperature at about 0° C., 335 g of 4'-butoxy-3'-methoxy-3-benzylidene camphor. When the product has dissolved, 0.1 g of sodium nitrite and 102 g of N-hydroxymethyl acrylamide are added.

The reaction mixture is stirred for 2 hours at 0° C. and is then slowly poured into ice water.

The gummy precipitate that forms slowly hardens.

The hardened precipitate is filtered, washed several times with water and dried under a vacuum, yielding 410 g of the expected product in the form of a whitish powder having the following properties:

| Melting point: 55° C. | | | | |
|---|---|---|---|---|
| Elemental analysis: | | | | |
| | C | H | N | O |
| Calculated (2H₂O) | 67.68 | 8.46 | 3.04 | 20.82 |
| Found (2H₂O) | 67.48 | 8.48 | 3.00 | 20.67 |
| U.V. Spectra (chloroform) | | | | |
| λ max: 331 nm | | | | |
| $a_s$ = 30 | | | | |

NMR¹H spectrum, CdCl₃/TMS conforms to the structure.

EXAMPLE 2

Preparation of poly-(2'-acrylamidomethyl-4'-butoxy-5'-methoxy-3-benzylidene camphor)

(a) Polymerization initiated by a H₂O₂-ascorbic acid system

At 80° C., 100 g of 2'-acrylamidomethyl-4'-butoxy-5'-methoxy-3-benzylidene camphor obtained in Example 1(b) are dissolved in 200 g of isopropanol and 15 g of 30% H₂O₂. There is then added over a 2 hour 40 minute period at 80° C., a solution of 10 g of ascorbic acid in 200 g of water. Reflux is maintained for 30 additional minutes. The reaction mixture is cooled to ambient temperature and the isopropanol is decanted. The polymer is washed with methanol, dried under vacuum and crushed, yielding 67 g of product in the form of a yellowish powder having the following properties:

| Elemental analysis: | | | | |
|---|---|---|---|---|
| | C | H | N | O |
| Calculated (0.75 H₂O) | 71.15 | 8.32 | 3.19 | 17.33 |
| Found (0.75 H₂O) | 71.05 | 8.29 | 3.10 | 16.97 |
| U.V. Spectrum: (chloroform) | | | | |
| λ max: 334 nm | | | | |
| $a_s$: 27 | | | | |

By chromatography on silica gel, solvent: CHCl₃, eluant hexane:ether (30:70) no free monomer is detected.

(b) Polymerization initiated by azobisisobutyronitrile

There are heated at reflux for 4 hours 100 g of 2'-acrylamidomethyl-4'-butoxy-5'-methoxy-3-benzylidene camphor and 10 g of azobisisobutyonitrile in 750 cm³ of toluene. The solvent is distilled off under reduced pressure, and the residue is redissolved in a minimum of anhydrous acetone. The expected polymer is obtained by precipitation in hexane, yielding 90 g of yellow powder having the following characteristics:

U.V. Spectrum (chloroform)
λ max: 332 mn
$a_s = 28$

EXAMPLES 3 TO 6

(a) In accordance with procedures analogous to those of Example 1(b), there have been prepared various 3'-acrylamidomethyl-4'-alkoxy-3-benzylidene camphors of the formula $CH_2=CO-NH-CH_2-X$ wherein X represents a group of formula II attached at the 3' position to the acrylamidomethyl group, with $R^2$ representing $-O-C_4H_9$, $-O-C_6H_{13}$, $-O-C_8H_{17}$ or $-O-C_{12}H_{25}$ and $R^1$ representing hydrogen.

The properties of these compounds are given in Table 1 below:

TABLE 1

| | | U.V. Spectrum (CH₂Cl₂) | | Elemental Analysis | | | | | | |
|---|---|---|---|---|---|---|---|---|---|---|
| | | | | Calculated % | | | | Found % | | |
| Ex | $R^2$ | max (nm) | $a_s$ | C | H | N | O | C | H | N | O |
| | | | | $C_{25}H_{33}NO_3$ | | | | | | | |
| 3a | $-OC_4H_9$ | 312 | 47 | 75.95 | 8.35 | 3.54 | 12.15 | 76.01 | 8.32 | 3.50 | 12.16 |
| | | | | $C_{27}H_{37}NO_3$ | | | | | | | |
| 4a | $-OC_6H_{13}$ | 313 | 46 | 76.55 | 8.80 | 3.30 | 11.73 | 76.66 | 8.97 | 3.36 | 11.01 |
| | | | | $C_{29}H_{41}NO_3.0.5H_2O$ | | | | | | | |
| 5a | $-OC_8H_{17}$ | 315 | 51 | 75.59 | 9.22 | 3.06 | 12.14 | 75.65 | 9.13 | 3.04 | 12.17 |
| | | | | $C_{33}H_{49}NO_3$ | | | | | | | |
| 6a | $-OC_{12}H_{25}$ | 314 | 42 | 78.11 | 9.66 | 2.76 | 9.47 | 78.21 | 9.55 | 2.81 | 9.41 |

(b) In accordance with procedures analogous to those described in example 2(a), there have been prepared various poly(3'-acrylamidomethyl-4-alkoxy-3-benzylidene camphor) homopolymers constituted by units of formula I wherein $R^2$ represents $-O-C_4H_9$, $-O-C_6H_{13}$, $-O-C_8H_{17}$ or $-O-C_{12}H_{25}$, and $R^1$ represents hydrogen.

The properties of these polymers are given in Table 2, below:

TABLE 2

| | | U.V. Spectrum (CH₂Cl₂) | | Elemental Analysis | | | | | | |
|---|---|---|---|---|---|---|---|---|---|---|
| | | | | Calculated % | | | | Found % | | |
| Ex | $R^2$ | max (nm) | $a_s$ | C | H | N | O | C | H | N | O |
| | | | | $C_{25}H_{33}NO_3.0.5\ H_2O$ | | | | | | | |
| 3 | $-OC_4H_9$ | 315 | 43 | 74.26 | 8.42 | 3.47 | 13.86 | 74.24 | 8.37 | 3.43 | 13.96 |
| | | | | $C_{27}H_{37}NO_3.0.25\ H_2O$ | | | | | | | |
| 4 | $-OC_6H_{13}$ | 316 | 47 | 75.79 | 8.71 | 3.27 | 12.16 | 75.92 | 8.86 | 3.20 | 12.31 |
| | | | | $C_{29}H_{41}NO_3.0.25\ H_2O$ | | | | | | | |
| 5 | $-OC_8H_{17}$ | 315 | 47 | 76.40 | 9.11 | 3.07 | 11.42 | 76.18 | 9.10 | 3.12 | 11.66 |
| | | | | $C_{33}H_{49}NO_3.0.25\ H_2O$ | | | | | | | |
| 6 | $-OC_{12}H_{25}$ | 315 | 35 | 77.42 | 9.68 | 2.74 | 10.17 | 77.43 | 9.75 | 2.49 | 10.54 |

EXAMPLE 7

Preparation of an acrylamidomethyl 3-benzylidene camphor/3'-acrylamidomethyl-4'-hexyloxy-3-benzylidene camphor copolymer There is heated at reflux a mixture of 21.6 g of acrylamidomethyl-3-benzylidene camphor, 28.3 g of 3'-acrylamidomethyl-4'-hexyloxy-3-benzylidene camphor and 7.5 g of 30% $H_2O_2$, in 100 g of isopropanol. There is then slowly added over a 3 hour period a solution of 5 g of ascorbic acid in 50 g of water. After this introduction, the reaction mixture is stirred again for 30 minutes at reflux. The reaction mixture is then cooled and the polymer that has formed is decanted. After washing with methanol, filtering and drying, 43 g of a copolymer having the following properties are obtained.

| Elemental analysis: $(C_{48}H_{62}N_2O_5.H_2O)_n$ | | | | |
|---|---|---|---|---|
| | C | H | N | O |
| Calculated: | 75.01 | 8.49 | 3.60 | 12.89 |
| Found: | 75.39 | 8.38 | 3.66 | 12.57 |

U.V. Spectrum
λ max: 302 nm
$a_s = 45$

Examples of Cosmetic Compositions

Example I

A milk (oil-in-water emulsion) having the following composition is prepared

| | |
|---|---|
| Polymer of example 7 | 1.5 g |
| Polymer of example 2a | 1.5 g |
| Cetyl stearyl alcohol | 1.6 g |
| Cetyl stearyl alcohol oxyethylenated with 33 moles of ethylene oxide | 6.4 g |
| Mixture of glycerol mono and distearate, sold under the trade name GELOL by Gattefosse | 3.5 g |
| Benzoate of $C_{12}-C_{15}$ alcohols, sold under the trade name FINSOLV TN by Finetex | 15 g |
| Petrolatum oil | 3.5 g |
| Propylene glycol | 12 g |
| 2-ethylhexyl paraaminobenzoate | 3 g |
| Preservative | 0.2 g |
| Perfume | 0.3 g |
| Demineralized water, sufficient amount for | 100 g |

The emulsion is prepared in the following manner:

Phase A, which consists of the polymers of Examples 8 and 2a, cetyl stearyl alcohol, cetyl stearyl alcohol oxyethylenated with 33 moles of ethylene oxide, glycerol mono and distearate, the benzoate of $C_{12}-C_{15}$ alcohols, petrolatum oil and 2-ethylhexyl paraaminobenzoate, is heated to 85° C. on a water bath.

Phase B, which consists of propylene glycol and water, is heated to 85° C. on a water bath.

Phase A is then poured into Phase B with vigorous stirring for 10 minutes. Stirring is then abated and at a temperature of 40° C. the preservative and perfume are added. The temperature of the emulsion is permitted to return to ambient temperature under moderate stirring.

Example II

In a similar fashion a milk having the following composition is prepared:

| | |
|---|---|
| Polymer of Example 2b | 3 g |
| Polymer of Example 2a | 2 g |
| Oleocetyl alcohol oxyethylenated with 30 moles of ethylene oxide | 6 g |
| Stearyl alcohol | 4 g |
| FINSOLV TN | 15 g |
| Oleyl alcohol | 4 g |
| Sorbitol, 70% | 16 g |
| Preservative | 0.2 g |
| Perfume | 0.3 g |
| Demineralized water, sufficent amount for | 100 g |

Example III

A thick oil having the following composition is prepared:

| | |
|---|---|
| Polymer of Example 4 | 3 g |
| 2-ethylhexyl paramethoxy-cinnamate | 3 g |
| FINSOLV TN | 26 g |
| Silica, sold under the trade name "AEROSIL R 972" by Degussa | 7 g |
| Cyclotetradimethyl siloxane | 10 g |
| Isopropyl myristate, sufficient amount for | 100 g |

Example IV

A cream in the form of a water-in-oil emulsion having the following composition is prepared:

| | |
|---|---|
| Polymer of Example 4 | 5 g |
| Magnesium stearate | 3.5 g |
| Octyl dodecanol | 10 g |
| Hydrogenated lanolin sold under the trade name "Hydrolan H" by Onyx | 1.5 g |
| Light lanolin | 4 g |
| Beeswax | 4.5 g |
| Sorbitan sesquioleate | 4.5 g |
| FINSOLV TN | 15 g |
| Petrolatum oil | 10 g |
| Preservative | 0.2 g |
| Demineralized water, sufficent amount for | 100 g |

Example V

An oil having the following composition is prepared:

| | |
|---|---|
| Polymer of Example 7 | 3.8 g |
| Palmitic ester of 2-ethylhexyl glyceryl ether | 30 g |
| Cyclotetradimethyl siloxane | 20 g |
| Perfume | 0.2 g |
| FINSOLV TN, sufficient amount for | 100 g |

What is claimed is:

1. A cosmetic composition for protecting the skin against ultraviolet radiations having wavelengths ranging from 315–340 nm comprising in a cosmetically acceptable vehicle suitable for topical application to the skin an ultraviolet-absorbing polymer having units of formula I

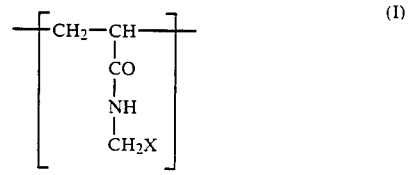

wherein

X is a group derived from the benzylidene-bornanone of formula II:

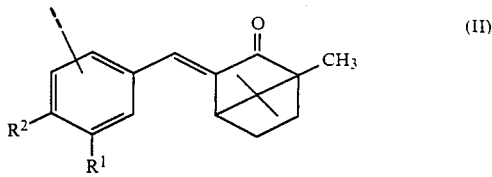

wherein $R^1$ represents hydrogen or $C_1$–$C_{12}$ alkoxy and $R^2$ represents $C_4$–$C_{12}$ alkoxy, said polymer being present in an amount ranging from 0.2 to 20 weight percent based on the total weight of said composition.

2. The cosmetic composition of claim 1 wherein $R^1$ represents hydrogen, methoxy or butoxy.

3. The cosmetic composition of claim 1 wherein $R^2$ represents butoxy, hexyloxy, octyloxy or dodecyloxy.

4. The cosmetic composition of claim 1 wherein said polymer also contains units of formula I':

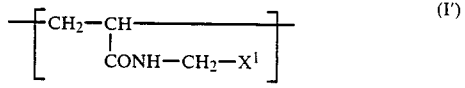

wherein $X^1$ represents a group derived from bornanone of formula II':

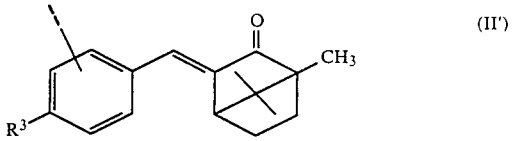

wherein $R^3$ represents hydrogen or $C_1$–$C_4$ alkyl.

5. The cosmetic composition of claim 1 wherein said polymer contains at least 5 mole percent of the units of formula I.

6. The cosmetic composition of claim 4 wherein the mole ratio of units of formula I to the units of formula I' ranges from 5:95 to 95:5, respectively.

7. The cosmetic composition of claim 1 wherein said polymer has a molar mass ranging from 1,000 to 1,000,000.

8. The cosmetic composition of claim 1 wherein said polymer has a molar mass ranging from 1,500 to 100,000.

9. A process for protecting human skin from sunburn comprising applying thereto the cosmetic composition of claim 1 in an amount effective to protect said skin against ultraviolet radiations ranging from 315–340 nm.

* * * * *